US012276631B2

(12) United States Patent
Kantack et al.

(10) Patent No.: US 12,276,631 B2
(45) Date of Patent: Apr. 15, 2025

(54) PARALLEL CLOCK SALINITY SENSOR

(71) Applicant: The Johns Hopkins University, Baltimore, MD (US)

(72) Inventors: Nicholas R. Kantack, Cambridge, MA (US); Jennifer S. Benzing, Baltimore, MD (US); Tessa B. VanVolkenburg, Ellicott City, MD (US); Zhiyong Xia, Rockville, MD (US); Spencer A. Langevin, Columbia, MD (US); Daniel S. Ayoub, Columbia, MD (US)

(73) Assignee: The Johns Hopkins University, Baltimore, MD (US)

( * ) Notice: Subject to any disclaimer, the term of this patent is extended or adjusted under 35 U.S.C. 154(b) by 511 days.

(21) Appl. No.: 17/671,809

(22) Filed: Feb. 15, 2022

(65) Prior Publication Data

US 2022/0404305 A1   Dec. 22, 2022

Related U.S. Application Data

(60) Provisional application No. 63/211,149, filed on Jun. 16, 2021.

(51) Int. Cl.
*G01N 27/22* (2006.01)
*G01N 33/18* (2006.01)
(Continued)

(52) U.S. Cl.
CPC ........... *G01N 27/226* (2013.01); *G01N 33/18* (2013.01); *G06F 1/10* (2013.01); *H03K 5/24* (2013.01)

(58) Field of Classification Search
CPC .. G01N 27/226; G01N 27/227; G01N 27/228; G01N 27/301; G01N 33/18; G06F 1/10; H03K 5/24
See application file for complete search history.

(56) References Cited

U.S. PATENT DOCUMENTS 4,549,141 A * 10/1985 Teass, Jr. ............... G01N 27/06
340/603
7,038,470 B1 * 5/2006 Johnson ............... G01N 27/226
250/390.05
(Continued)

OTHER PUBLICATIONS

T. R. Kuphaldt, "The S-R Latch," Allaboutcircuits.com, Feb. 17, 2015. https://www.allaboutcircuits.com/textbook/digital/chpt-10/s-r-latch/ (accessed online Jan. 3, 2025).
(Continued)

*Primary Examiner* — Suman K Nath
(74) *Attorney, Agent, or Firm* — Sung T. Kim

(57) ABSTRACT

A sensor for measuring ocean water salinity is described. The sensor may include a measurement clock circuit, a control clock circuit, and a comparator circuit. The measurement clock circuit, having an output that varies with salinity of a fluid, may have a first circuit architecture that includes a capacitive gap assembly that permits a fluid to flow into a gap between two electrodes of the capacitive gap assembly. The control clock circuit, having an output that does not vary with salinity of the fluid, may have a second circuit architecture comprising a capacitor. The comparator circuit may be configured to compare the controlled clock output to the measured clock output over a duration of time to determine a salinity measurement of the fluid. The first circuit architecture may differ from the second circuit architecture in that an electrically connected position of the capacitive gap assembly within the first circuit architecture is the electrically connected position of the capacitor within the second circuit architecture.

22 Claims, 8 Drawing Sheets

(51) Int. Cl.
  *G06F 1/10*   (2006.01)
  *H03K 5/24*   (2006.01)

(56) References Cited

U.S. PATENT DOCUMENTS

2004/0178804 A1* 9/2004 Allen .................. G01N 27/221
                                                324/662
2005/0077901 A1* 4/2005 Delhomme ............ G01N 33/18
                                                 324/324

OTHER PUBLICATIONS

V. G. Kapoor, "Race condition in digital circuits," Aug. 2013. https://vlsiuniverse.blogspot.com/2013/08/race-condition.html (accessed online Jan. 3, 2025).
"Race conditions," CircuitVerse. https://learn.circuitverse.org/docs/seq-design/race-conditions.html (accessed online Jan. 3, 2025).
R. Anand, Digital Electronics (Digital Logic Design), 2nd ed. New Delhi, India: Khanna Book Publishing Co. (P) Ltd., 2014, pp. 284-285.
S. Huang et al., "Race-condition-aware clock skew scheduling," Proceedings. 42nd Design Automation Conference, 2005, Anaheim, CA, USA, pp. 475-478, doi: 10.1109/DAC.2005.193856.
S. Loganayagi et al., "Glitchless Digitally Contrlled Delay Lines For Power Optimization," International Journal For Technological Research In Engineering, vol. 1, No. 9, pp. 1018-1020, May 2014, Accessed online: Jan. 3, 2025. https://ijtre.com/images/scripts/2014010973.pdf.
J. Stinson, "Lecture 10 Circuit Pitfalls." Accessed online: Jan. 3, 2025. Available: https://web.stanford.edu/class/archive/ee/ee371/ee371.1066/lectures/Old/Older/lect_10_ckt_pitfalls_1up.pdf.

* cited by examiner

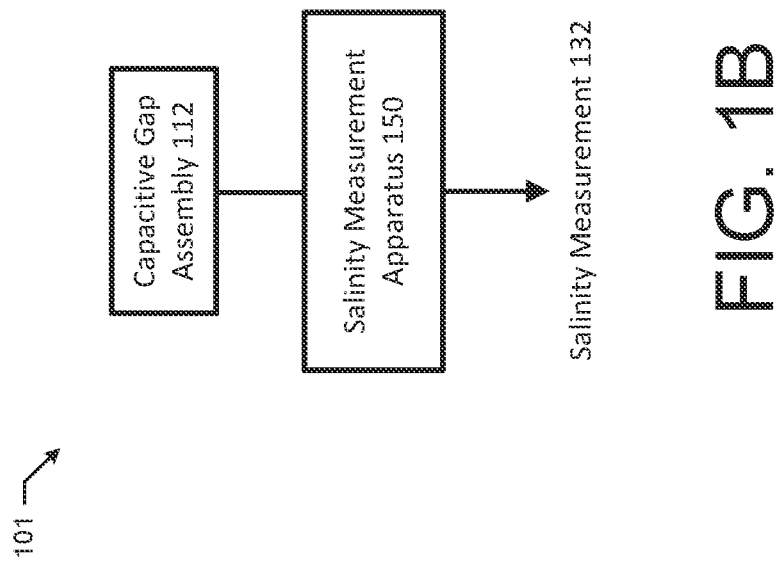

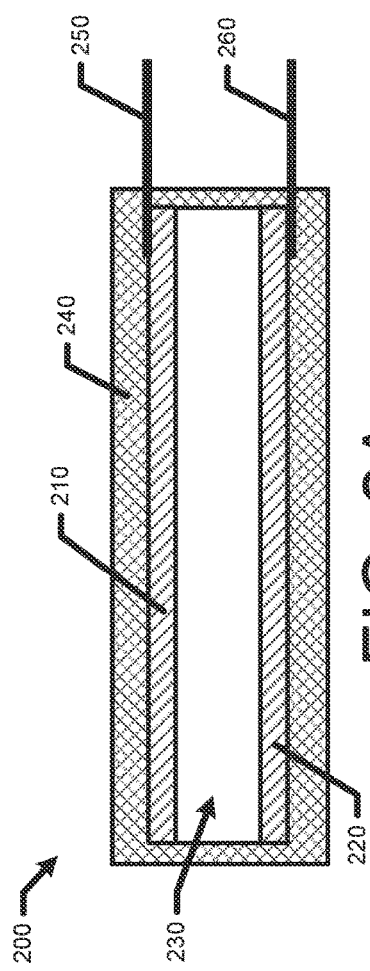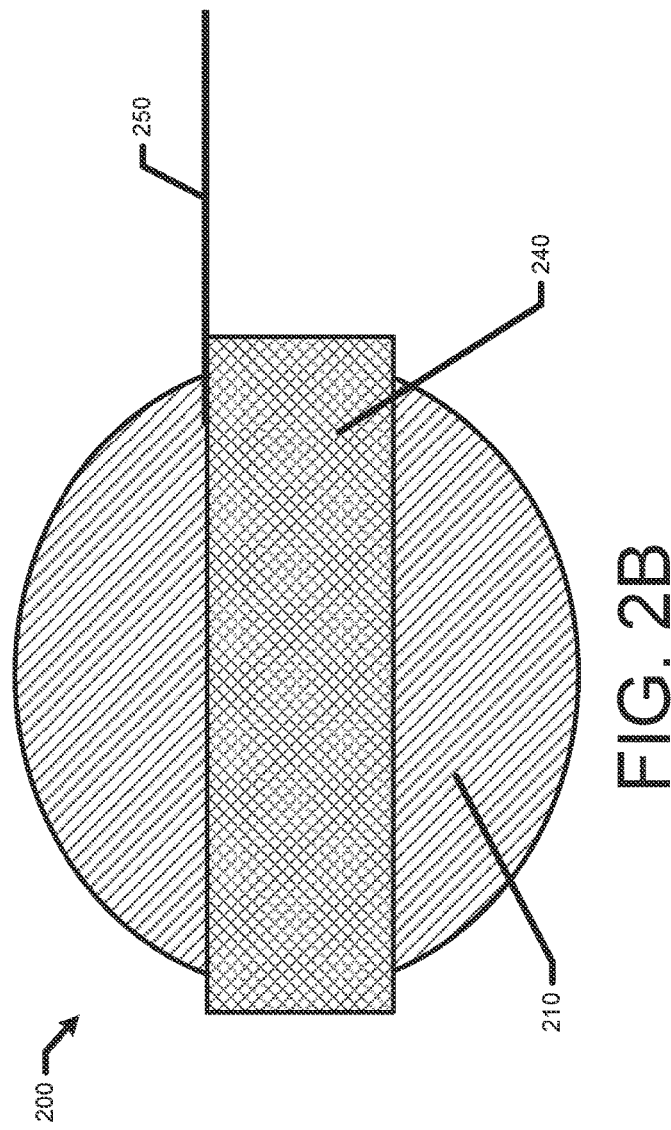

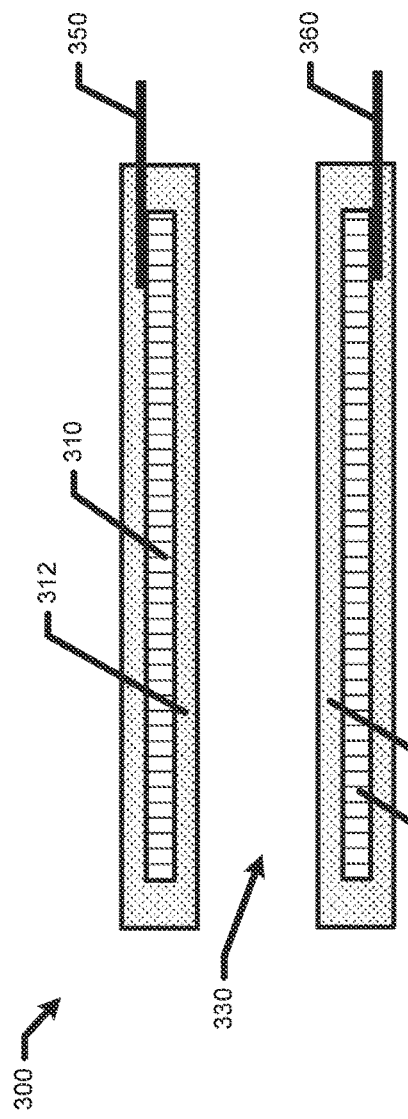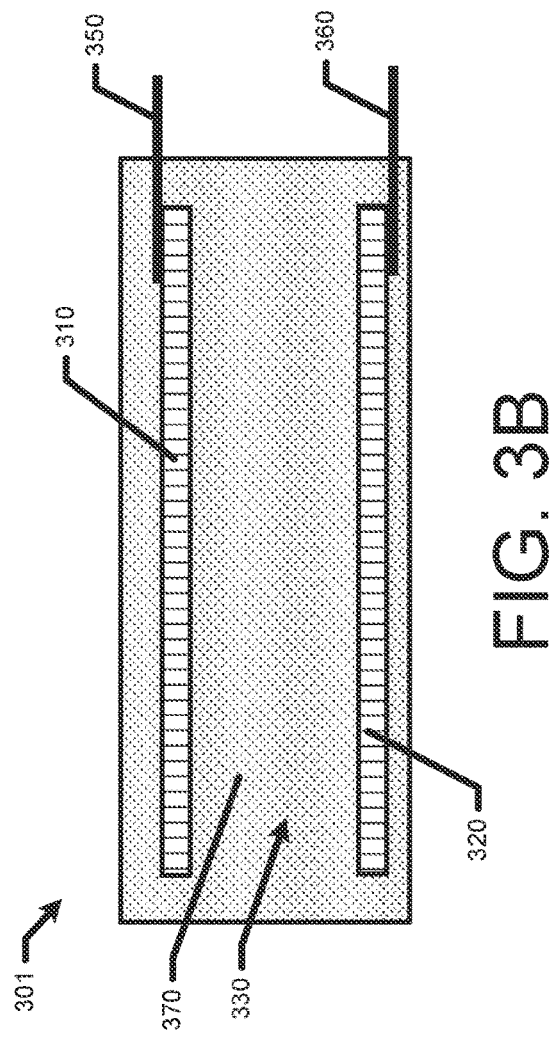
FIG. 3A
FIG. 3B

PARALLEL CLOCK SALINITY SENSOR

CROSS-REFERENCE TO RELATED APPLICATIONS

This application claims the benefit of U.S. Provisional Patent Application No. 63/211,149 filed on Jun. 16, 2021, the entire contents of which are hereby incorporated herein by reference.

STATEMENT REGARDING FEDERALLY SPONSORED RESEARCH OR DEVELOPMENT

This invention was made with Government support under Contract No. N00014-19-1-2654 awarded by the United States Department of the Navy. The Government has certain rights in the invention.

TECHNICAL FIELD

Exemplary embodiments generally relate to ocean monitoring and measurement systems, and more specifically relate to ocean salinity sensors and materials technologies to facilitate salinity measurements.

BACKGROUND

The implementation of ocean sensors for measuring and monitoring the ocean environment has provided a plethora of data for analysis by oceanographers. Sensor data can include water temperature, pressure, water current, and wind speeds. Additionally, the measure of ocean water salinity also provides important insights into weather patterns, changes in biodiversity, and the evolution of currents.

Ocean salinity is typically measured by passing current between two submerged electrodes or induction coils. The inductive coupling between, for example, two wire coils may also be used to make measurements of ocean water salinity. However, in implementation, such conductive and inductive modes of ocean salinity sensing often suffer from a number of disadvantages. For example, the electrodes and/or the housing may be subjected to galvanic corrosion and marine fouling, which can lead to unreliable conductivity or inductance measurements, which in turn causes inaccurate salinity measurements. Further, high accuracy inductive salinity sensors are expensive, can be bulky and rigid, and are therefore inconvenient to use. Additionally, due to reliance on unconfined magnetic fields to take the measurements, induction measurements can be readily affected by nearby objects, particularly conductive objects, such as ship hulls, which can affect the accuracy of the salinity measurements raising data reliability concerns.

Accordingly, there is a need for improvement and innovation in the area of oceanographic sensors. In particular, improvements in reliability, size, weight, power, and/or cost are desired.

BRIEF SUMMARY OF SOME EXAMPLES

According to some example embodiments, a sensor for measuring ocean water salinity is described. The sensor may comprise a measurement clock circuit having a first circuit architecture comprising a capacitive gap assembly that permits a fluid to flow into a gap between two electrodes of the capacitive gap assembly. The measurement clock circuit may have a measured clock output that varies with a salinity of the fluid. The sensor may also comprise a control clock circuit having a second circuit architecture comprising a capacitor. The control clock circuit may have a controlled clock output that does not vary with the salinity of the fluid. The sensor may also comprise a comparator circuit configured to compare the controlled clock output to the measured clock output over a duration of time to determine a salinity measurement of the fluid. Further, the first circuit architecture may differ from the second circuit architecture in that an electrically connected position of the capacitive gap assembly within the first circuit architecture is the electrically connected position of the capacitor within the second circuit architecture.

According to some example embodiments, a sensor for measuring ocean water salinity is described. The sensor may comprise a capacitive gap assembly comprising two electrodes that form a gap there between. The sensor may also comprise a salinity measurement apparatus operably coupled to the capacitive gap assembly. The salinity measurement apparatus may be configured to determine a salinity measurement of a fluid disposed in the gap between the two electrodes based on a displacement current between the electrodes. The electrodes may be fully or partially coated with a hydrogel material.

According to some example embodiments, a method is described. The example method may comprise generating a measured clock output that varies based on a salinity of a fluid disposed within a gap between two electrodes of a capacitive gap assembly. In this regard, the measured clock output may be generated by a measurement clock circuit having a first circuit architecture comprising the capacitive gap assembly. The method may also comprise generating a control clock output that does not vary based on the salinity of the fluid. In this regard, the control clock output may be generated by a control clock circuit having a second circuit architecture comprising a capacitor. The first circuit architecture may differ from the second circuit architecture in that an electrically connected position of the capacitive gap assembly within the first circuit architecture is the electrically connected position of the capacitor within the second circuit architecture. The example method may further comprise comparing, by a comparator circuit, the controlled clock output to the measured clock output over a duration of time to determine a salinity measurement of the fluid.

BRIEF DESCRIPTION OF THE SEVERAL VIEWS OF THE DRAWING(S)

Having thus described some example embodiments in general terms, reference will now be made to the accompanying drawings, which are not necessarily drawn to scale, and wherein:

FIG. 1B illustrates another example salinity sensor according to some example embodiments;

FIG. 2A illustrates side view of an example capacitive gap assembly according to some example embodiments;

FIG. 2B illustrates top view of an example capacitive gap assembly according to some example embodiments;

FIG. 3A illustrates an example capacitive gap assembly with hydrogel coatings according to some example embodiments;

FIG. 3B illustrates an example capacitive gap assembly with hydrogel material extending through the gap according to some example embodiments;

DETAILED DESCRIPTION

Figure 1A:
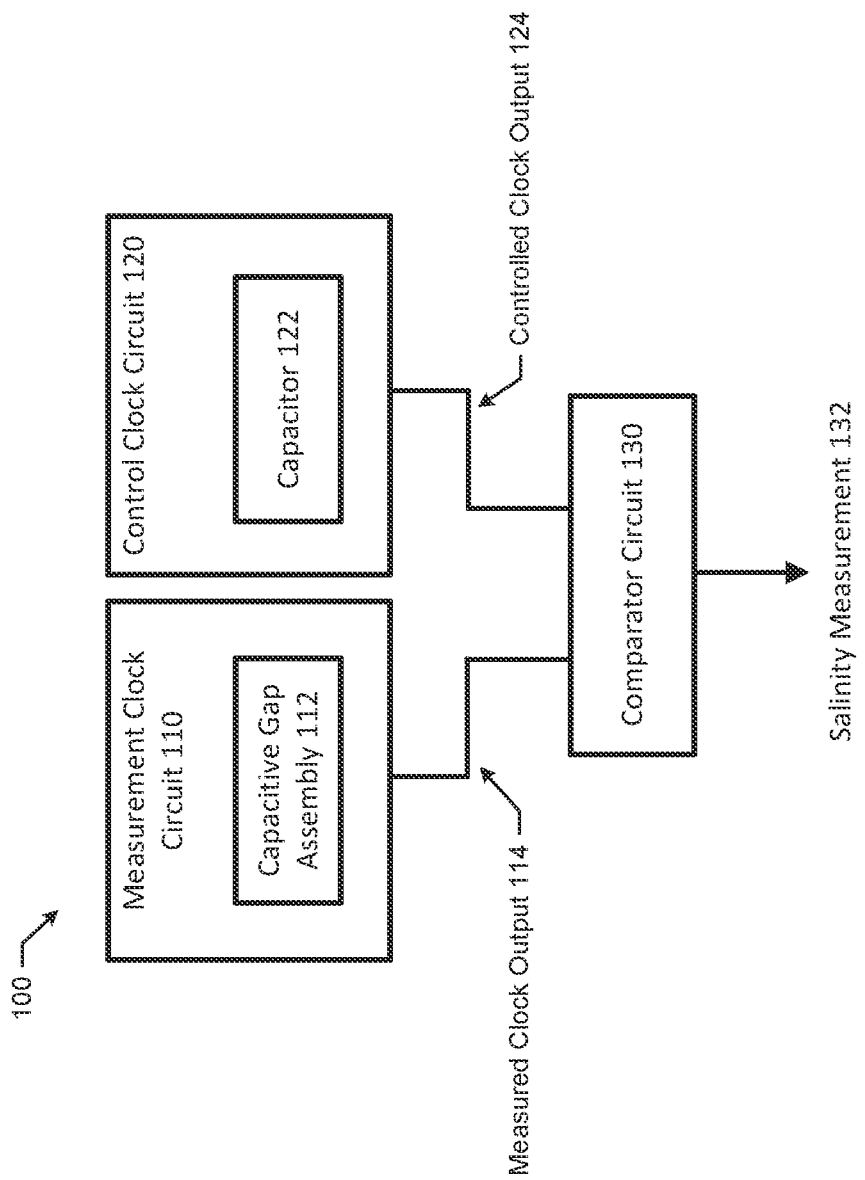
FIG. 1A illustrates an example salinity sensor according to some example embodiments.

Some example embodiments now will be described more fully hereinafter with reference to the accompanying drawings, in which some, but not all example embodiments are shown. Indeed, the examples described and pictured herein should not be construed as being limiting as to the scope, applicability or configuration of the present disclosure. Rather, these example embodiments are provided so that this disclosure will satisfy applicable legal requirements. Like reference numerals refer to like elements throughout.

According to various example embodiments, systems and methods are provided for performing, and facilitating the performance of, salinity measurements, for example, in an ocean environment. According to some example embodiments, a salinity sensor can be realized that does not suffer from the disadvantages of conventional inductive and conductive sensors and can accurately measure salinity while being uniquely resilient in oceanic environments.

Various example embodiments operate to measure salinity in seawater by measuring the capacitance across a gap of a capacitive gap assembly that can be submerged in, and filled with, seawater. For such capacitive sensors, direct current (DC) travelling across the gap is not needed to measure the capacitance. In this regard, according to some example embodiments, a displacement current approach may be used for determining the capacitance, which does not involve a current passing from one of the electrodes to the other electrode. Since no electric current passes across the gap, the electrodes that form the gap need not be highly conductive on their external surfaces, which can allow a coating to be applied to the electrodes that could inhibit the growth of biological organisms on the electrodes. Such coatings, which includes conformal coatings that conform to the shape of the electrodes, may protect the electrodes from the corrosion and marine fouling that often occur in oceanic environments. Such corrosion and fouling would otherwise have significant negative impacts on the performance, durability, and useable lifespan of the electrodes. As such, according to some example embodiments, designs provided herein may combine fouling resistance with highly stable and sensitive capacitance measurements for constructing and implementing a reliable and accurate salinity sensor.

In this regard, according to some example embodiments, coated capacitor electrodes may be utilized in a high precision salinity sensor that leverages detuning (i.e., a change in frequency) between two nearly identical, parallel clock circuits, that output respective clock-pulse waveforms, to determine the effect of salinity on a measured clock, relative to a control clock. The clock circuits may be implemented as astable multivibrator circuits. The structural difference between the clock circuits may, according to some example embodiments, be that a control clock circuit which may include a capacitor in the form of a singularly packaged capacitor (e.g., an off-the-shelf ceramic, film, electrolytic, or the like) and a counterpart measurement clock circuit which may be identical with the exception of the capacitor being replaced with a capacitive gap assembly that interfaces with (i.e., is submerged into) the seawater for salinity detection. The control clock circuit may provide a regular pulsed clock output that has a frequency based on the components of circuit (e.g., passive components). The measurement clock circuit, on the other hand, will provide a measured clock output with a frequency that varies with the salinity of the water. In this regard, the capacitive gap assembly may comprise two electrodes that form a gap there between that seawater can ingress. The concentration of salt or the salinity in the seawater may affect the capacitance of the capacitive gap assembly to change a resonant frequency of the measurement clock circuit as compared to the reference clock. Moreover, the changes in salt concentration between electrodes of the capacitive gap assembly can result in a shift in the frequency of the measurement clock circuit. As such, the effect of the water salinity on the measured clock output can be isolated relative to the control clock output of the control clock circuit to determine a frequency difference that can be used to determine seawater salinity. According to some example embodiments, the frequencies output by the circuits may be measured in a number of different ways, with one way being to count relative clock events or pulses. For example, the rate of the pulses for the measurement clock circuit may change, and therefore respective counter circuits may be used to compare a number of clock pulses output by the measurement clock circuit and the control clock circuit over a set duration of time. This difference in the pulse counts can then be converted into salinity measurement units.

According to some example embodiments, the electrodes of the capacitive gap assembly for use in a salinity sensor may be coated with a desired material to increase the electrodes' charge surface area and inhibit marine fouling of the electrodes, as well as, the overall device. The application of a hydrogel material to the electrodes may be performed for these purposes. The hydrogel material may be, according to some example embodiments, a matrix of hydrophilic polymers that can retain water as a porous structure while maintaining structural integrity. The hydrogel matrix structure may be three-dimensional and may be formed via chemical or physical crosslinking or entanglement of polymer chains. According to some example embodiments, a hydrogel material may include at least fifty percent of water by weight. According to some example embodiments, a hydrogel material may be flexible and have a particular affinity for water due to the inclusion of hydrophilic groups in the structure, such as, for example, —$NH_2$, —COOH, —OH, —$CONH_2$, —CONH, —$SO_3H$ or other functional groups with similar polarity features. By providing certain stimuli to a hydrogel material (e.g., thermal, electrical, electromagnetic, volumetric, chemical, etc.), a phase change may be triggered that may cause the hydrogel material to conform to the shape of the electrodes, and, for example, be disposed in the gap between the electrodes. The inclusion of the hydrogel material on the electrodes of the sensor dramatically amplifies the salt-induced permittivity change between the electrodes. According to some example embodiments, hydrogel materials can also be designed or be tuned with biological material interactions to inhibit marine fouling in oceanic environments. Accordingly, the inclusion of a hydrogel material to the system may increase the change in capacitance due to presence of salinity in the water retained by the hydrogel material and may also perform an antifouling function.

Example embodiments offer a number of further advantages over conventional salinity sensor solutions. For example, because parallel clock circuits are implemented together, external environmental influences are mitigated since the circuits are both similarly affected. Additionally, a small frequency shift in the measurement clock circuit can be readily detected (without high-speed sampling) by merely extending the measurement duration. Yet another advantage is the absence of a microprocessor as a requirement to perform the measurements, which reduces cost and size in an application (i.e., oceanic salinity sensing) where constraints on size and power are common. Further, according to some example embodiments, a salinity sensor may be constructed in accordance with some example embodiments that can be sensitive to frequency shifts on the measurement clock circuit that are as small as 0.012%, which supports salinity sensitivity at 0.05 parts per thousand.

Having provided a description of some example embodiments, FIGS. 1A and 1B will be described which include block diagrams of example salinity sensors. FIG. 1A illustrates a salinity sensor 100 that comprises a measurement clock circuit 110, a control clock circuit 120, and a comparator circuit 130. According to some example embodiments, the circuitry of the salinity sensor 100 may be housed in a common housing to ensure that any environmental effects are experienced by both the measurement clock circuit 110 and the control clock circuit 120. Additionally, as further described below, the measurement clock circuit 110 and the control clock circuit 120 may be constructed with identical respective structures, with the exception of the capacitor 122 of the control clock circuit 120 being substituted with a capacitive gap assembly 112. The measurement clock circuit 110 and the control clock circuit 120 may leverage a resistor-capacitor (RC) constant to form a resonant circuit that outputs pulses at a frequency based on the resistance and capacitance values.

As such, the measurement clock circuit 110 may be formed as a resonating circuit that outputs a clock signal in the form of the measured clock output 114. The measurement clock circuit 110 may be formed, according to some example embodiments, as any type of clock circuit. According to some example embodiments, the clock circuit architecture may comprise a collection of passive components that operate together to output a repeating, clock-type waveform that has a frequency that is based on a capacitance between the electrodes of the capacitive gap assembly 112 of the measurement clock circuit 110. An example clock circuit that may be implemented in this context may be an astable multivibrator circuit. An astable multivibrator circuit may be a circuit that is not stable in any one state, but is constantly transitioning from one state into another state. As a result, the circuit outputs a waveform that is a repeating high/low pattern having a frequency based on the capacitance between the electrodes of capacitive gap assembly 112. In this manner, the waveform output of the astable multivibrator circuit may have, for example, a sawtooth-type shape. Regardless of the type of clock circuit, the measurement clock circuit 110 may output a clock-type waveform that has a repeating high and low (e.g., voltage) value with a frequency that changes with the changes in capacitance of capacitive gap assembly 112. Because the capacitance of the capacitive gap assembly 112 is a function of the salinity of water that is interacting with the capacitive gap assembly 112, the measured clock output 114 from the measurement clock circuit 110 can be indicative of the salinity.

The architecture of the control clock circuit 120 may be identical to the measurement clock circuit 110, with the exception of the capacitor 122 (e.g., an off-the shelf capacitor) may be substituted for capacitive gap assembly 112 at the same position within the common architecture of the clock circuits. As such, the control clock circuit 120 may have the architecture of, for example, an astable multivibrator circuit that is common with the measurement clock circuit 110. The control clock circuit 120 may therefore output a more predictable clock-type waveform, since the control clock circuit 120 does not include a variable element that is affected, for example, by the salinity of the water. As such, the control clock output 124 may be used as a control or base for comparison with the measured clock output 114 to determine a difference that can be attributed to the salinity in the water.

Accordingly, to determine this difference between the measured clock output 114 and the control clock output 124, a comparator circuit 130 may be used. The comparator circuit 130 may be a counter circuit that counts, for example, the high/low transitions in each of the measured clock output 114 and the control clock output 124 for comparison. According to some example embodiments, a portion of the comparator circuit 130 may be implemented to count transitions (e.g., high/low transitions or low/high transitions) in the measured clock output 114 for a duration of time, and another portion of the comparator circuit 130 may be implemented to count transitions (e.g., high/low transitions or low/high transitions) in the control clock output 124 over the same duration of time. The values of the measured counts and the control counts may be then be compared to determine an impact of the salinity of the water on the measured counts. According to some example embodiments, a count difference may be determined via a subtraction operation. Alternatively, a counting technique may be implemented where the duration of time for counting is determined as the time required for a most significant bit (MSB) or an overflow of the counting circuitry for control clock output 124 to go high (true). As such, the pin for the MSB may, according to some example embodiments, be used as a load input for a latch circuit to load the measured count in the latch circuit when the pin for the MSB of the counting circuity for control clock output 124 goes high (true). Accordingly, passive logic components may be used to perform the measurement, and therefore some example embodiments do not include or implement a microprocessor or a unitary oscillator (e.g., crystal oscillator) for use in determining the salinity measurement 132. A more specific implementation of some example implementations of the comparator circuit are described with respect to FIGS. 4 and 5 below.

According to some example embodiments, a count difference, as generated by the comparator circuit 130, may be output by the salinity sensor 100 as the salinity measurement 132. The clock difference is an implementation of a numerical approach and comparison of the pulse counts associated with the control clock output 124 and the measured clock output 114. Over a sufficiently long duration, a small change in frequency between the measurement clock circuit 110 and the control clock circuit 120 may result in a large difference in pulse counts. The count difference may be related to the salinity of the water based on a known correlation. As such, the known correlation may be used as a transfer function to convert the salinity measurement 132 as a count difference to a salinity value. The translation of the salinity measurement 132 to another usable value may be performed by the salinity sensor 100, but, alternatively, may be performed by a separate processing apparatus. In this regard, the salinity sensor 100 may be configured to transmit the salinity measurement 132 to the processing apparatus, or the salinity sensor 100 may be retrieved and a memory module that stores the salinity measurement 132 may be removed from salinity sensor 100 (e.g., as a memory stick) for installation in the processing apparatus for analysis.

Therefore, according to some example embodiments, the example salinity sensor 100 may comprise the measurement clock circuit 110 having a first circuit architecture that includes a capacitive gap assembly 112. The capacitive gap assembly 112 may permit a fluid (e.g., seawater) to flow into a gap between two electrodes of the capacitive gap assembly 112, as further described below. The measurement clock circuit 110 may have a measured clock output 114 that varies with a salinity of the fluid. The salinity sensor 100 may further comprise the control clock circuit 120 having a second circuit architecture comprising a capacitor 122. The control clock circuit 120 may have a control clock output 124 that does not vary with the salinity of the fluid. Additionally, the first circuit architecture may differ from the second circuit architecture in that an electrically connected position of the capacitive gap assembly 112 within the first circuit architecture is the same electrically connected position of the capacitor 122 within the second circuit architecture. The salinity sensor 100 may also include a comparator circuit 130 configured to compare the control clock output 124 to the measured clock output 114 over a duration of time to determine a salinity measurement of the fluid. According to some example embodiments, the first circuit architecture may be an astable multivibrator circuit and the second circuit architecture may also be an astable multivibrator circuit. A frequency of the measured clock output 114 may be based on a capacitance between the two electrodes, and the frequency may change due to changes in a salinity of the fluid within the gap.

FIG. 1B illustrates an alternative salinity sensor 101 according to some example embodiments. In this regard, the capacitive gap assembly 112 may be used directly or indirectly as a sensor element for the salinity sensor 101. A salinity measurement apparatus 150 may include various circuitry configured to determine a capacitance between the electrodes of the capacitive gap assembly 112 to generate the salinity measurement 132. For example, the configuration of the measurement clock circuit 110, the control clock circuit 120, and the comparator circuit 130 may be implemented as an example of a salinity measurement apparatus 150.

Now referring to FIGS. 2A to 3B, example capacitive gap assemblies are shown in accordance with some example embodiments. In this regard, FIG. 2A is a side view of an example capacitive gap assembly 200, and FIG. 2B is a top view of the capacitive gap assembly 200. In this regard, the capacitive gap assembly 200 may comprise a first electrode 210, a second electrode 220, a gap 230, a holding bracket 240, and leads 250 and 260. According to some example embodiments, the capacitive gap assembly 200 may implemented as a parallel-plate capacitor assembly, where the electrodes are embodied as parallel plates. Further, the capacitive gap assembly 200 may be the same or similar to the capacitive gap assembly 112, and the capacitive gap assembly 200 may be implemented in the same manner as capacitive gap assembly 112.

The first electrode 210 may be spaced apart from the second electrode 220 by the gap 230. The width of the gap 230 (i.e., the distance between the electrodes 220 and 230) may be selected such that the capacitance between to the electrodes 220 and 230 is within a desired range. The holding bracket 240 may engage with each of the first electrode 210 and the second electrode 220 to hold the electrodes in a position to define the desired gap 230. The first electrode 210 and second electrode 220 may be formed of a conductive material (e.g., a metal) and the first electrode 210 and second electrode 220 may operate together to form a type of parallel-plate capacitor assembly. In this regard, an external device to the capacitive gap assembly 200 may be configured to electrically couple to the first electrode 210 and the second electrode 220 via the lead 250 and the lead 260, respectively, to facilitate measuring a capacitance between the first electrode 210 and the second electrode 220. As mentioned above, the first electrode 210 and second electrode 220 may operate within an example system where the no current passes between the electrodes 210 and 220, but characteristics associated with the capacitance may be leveraged. As shown in FIG. 2A, the gap 230 may be accessible to seawater to flow into the capacitive gap assembly 200 and into the gap 230.

The electrodes 210 and 220 may take any shape, while still operating as parallel plates. In this regard, as shown in FIG. 2B, the electrodes 210 and 22 may have a circular shape. However, it is appreciated that the electrodes may be rectangular, square, oval, or the like. Additionally, the electrodes 210 and 220 may be formed of a material that has anti-corrosion features, such as stainless steel. According to some example embodiments, the electrodes 210 and 220 may be coated with an anti-corrosive non-conductive coating such as parylene-C.

Now referring to FIGS. 3A and 3B, example embodiments of a capacitive gap assembly 300 will now be described that include a hydrogel material. In this regard, similar to the structure of the capacitive gap assembly 200, the capacitive gap assembly 300 includes a first electrode 310 and a second electrode 320 that from a gap 330. The leads 350 and 360 facilitate electrical connection to the first electrode 310 and the second electrode 320 for implementation in the context of, for example, a salinity sensor. According to some example embodiments, the electrode 310 may include a hydrogel coating 312 and the electrode 320 may include a hydrogel coating 322. The hydrogel material used for the hydrogel coatings may be applied in a manner that conforms to the shape of the respective electrode. The hydrogel coatings 312 and 322 may operate to increase the space charge surface area for each of electrodes 310 and 320 to thereby increase the sensitivity of the capacitive gap assembly 300 to smaller changes in salinity. As stated above, the hydrogel material may be configured to absorb water into its structure. As such, this retention action of the hydrogel material can operate to pull seawater into close interaction with the electrodes 310 and 320 due to the hydrogel material's porous structure. In this regard, according to some example embodiments, the hydrogel material may comprise carbon nanotubes (e.g., single walled or multi-walled carbon nanotubes) embedded inside a network or lattice-type, three-dimensional structure. In this regard, the carbon nanotubes may be a single example of a conductive filler that may be used in accordance with some example embodiments. The conductive fillers may operate to increase the electrical conductivity of the hydrogel material. Another example of a conductive filler, according to some example embodiments, may be a conductive polymer or graphene or graphite or carbon black or other similar conductive fillers. According to some example embodiments, the hydrogel material may also comprise dyes and additives that, for example, increase electrical conductivity, protect the hydrogel from certain contaminants, increase adhesive properties with respect to seawater, or the like. Implementation of the hydrogel coating can also inhibit marine fouling of the electrodes 310 and 320 in an ocean environment.

Referring to FIG. 3B, an alternative capacitive gap assembly 301 is shown with a different structure. In this regard, the hydrogel material may be applied in such a manner that the hydrogel material fills the gap 330 and encapsulates the electrodes 310 and 320, and the gap 330, with the hydrogel structure 370. The hydrogel material may extend from the first electrode 310, through the gap, to the second electrode 320. Because the hydrogel material is porous and retains water, the gap 330 is still effectively present and the electrodes 310 and 320 can still be used to measure capacitance. Seawater may therefore be permitted to fill the gap 330 in the capacitive gap assembly 301, and be used in a salinity sensor as described herein.

Figure 4:
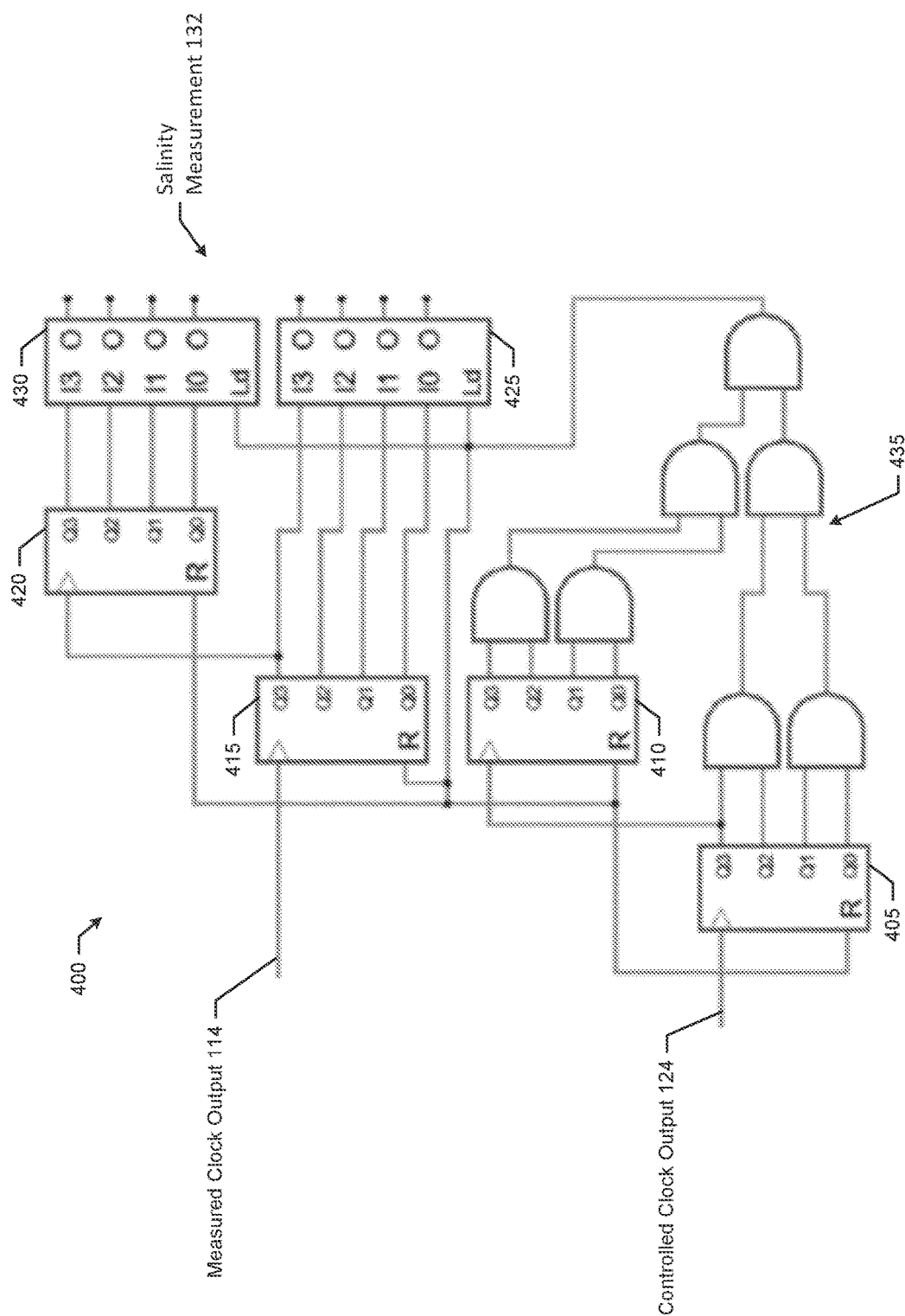
FIG. 4 illustrates schematic diagram for a comparator circuit according to some example embodiments.

Now referring to FIG. 4, an example implementation of the comparator circuit for a salinity sensor in accordance with some example embodiments is provided. In this regard, the comparator circuit 400 may be implemented as the comparator circuit 130 of the salinity sensor 100. As such, the measured clock output 114 and the control clock output 124 may be inputs to the comparator circuit 400. The comparator circuit 400 may also provide an output in the form of the salinity measurement 132.

The comparator circuit 400 may be implemented as a network of binary counters configured to determine a difference between a number of clock pulses in the measured clock output 114 over a duration of time and a number of clock pulses in the controlled clock output 124 over the same duration of time. In this regard, the comparator circuit 400 may be configured to operate as an implementation of two 8-bit counters and a latch for providing the output as the salinity measurement 132. In this regard, 4-bit counters 405 and 410 operate in association with the control clock output 124, and 4-bit counters 415 and 420 operate in association with the measured clock output 114.

First focusing on the operation related to the control clock output 124, the control clock output 124 is provided as a clock input to 4-bit counter 405. When the counter 405 accumulates counts to the point that the Most Significant Bit (MSB) (or Q3) is high (true), counter 410 increments due to the connection between Q3 and the clock of counter 410. As such, the combination of the 4-bit counter 405 and the 4-bit counter 410 forms an 8-bit counter for the control clock output 124. The AND gate network 435 comprises AND gates connected to each of the bits of the 8-bit counter for the control clock output 124. Therefore, when all of the bits are high (true), the output of the AND gate network 435 goes high (true). This output of the AND gate network 435 is used to the control the load pin on the latches 425 and 430 and to reset the counters 415 and 420. As such, the pulses on the control clock output 124 are counted until 11111111 is generated on the 8-bit counter output. As such, an overflow condition on the control counter can result in a latch and reset condition. Since the frequency of the waveform on the control clock output 124 is substantially constant, the 8-bit counter and the AND gate network 435 can operate to set the measurement duration of over which pulses on the measured clock output 114 will be counted.

Referring to the counters 415 and 420, the counters are connected to form an 8-bit counter for the measured clock output 114. As such, this 8-bit counter will accumulate a pulse count for the measured clock output 114 until the control clock output 124 count reaches 11111111 (overflow). At that time, the measured count on the 8-bit counter for the measured clock output 114 will be loaded into the 8-bit latch formed by the two 4-bit latches 425 and 430. Upon loading, the measured count can be provided as the salinity measurement 132. Additionally, because the output of the AND circuitry 435 is connected to the reset pins of all of the counters 405, 410, 415, and 420, the entire comparator circuit 400 can be reset and counting may begin anew until a next measured count is loaded.

Accordingly, the counters 415 and 420 form a measured counter where the measured clock output 114 is the input. Similarly, counters 405 and 410 with the AND gate network 435 form a control counter where the control clock output 124 is the input. An output of the control counter operates as a control signal to cause a measured count accumulated by the measured counter to be output and loaded into a latch that is formed by the latches 425 and 430. Additionally, the output of the control counter also operates as a reset signal for the measured counter.

Figure 5A:
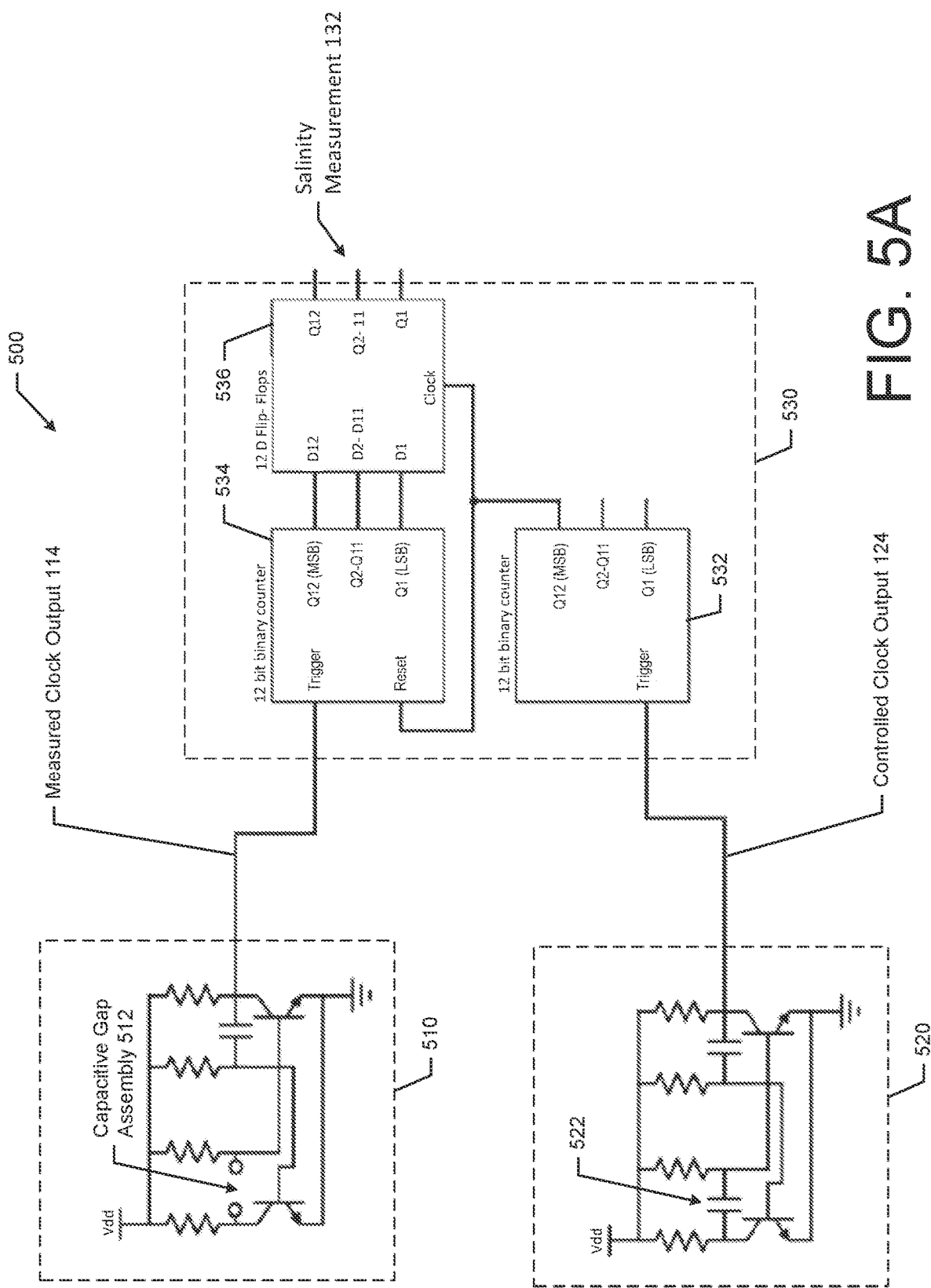
FIG. 5A illustrates a schematic diagram for another salinity sensor according to some example embodiments.

Now referring to FIG. 5A, an example salinity sensor 500 is provided. The salinity sensor 500 may comprise a measurement clock circuit 510, a control clock circuit 520, and a comparator circuit 530. As shown in FIG. 5A, the measurement clock circuit 510 and the control clock circuit 520 are identical clock circuits with the exception of a capacitive gap assembly 512 of the measurement clock circuit 510 being positioned in the same electrically connected location as the capacitor 522. The capacitor 522 may be, for example, a surface-mount capacitor on a circuit board. The measurement clock circuit 510 and the control clock circuit 520 are examples of clock circuits implemented as astable multivibrator circuits. Accordingly, the measurement clock circuit 510 operates in the same or similar manner as the measurement clock circuit 110 to generate the measured clock output 114 and the control clock circuit 520 operates in the same or similar manner as the control clock circuit 120 to generate the control clock output 124.

Because the capacitance of the capacitor 522 is fixed, the control clock 520 provides a repeating, periodic clock signal as the controlled clock output 124. The measurement clock 510, on the other hand, outputs the measured clock output 114 that is dependent upon the capacitive gap assembly 512. Accordingly, the measured clock output 114 and the control clock output 124 are inputs to the comparator circuit 530. The comparator circuit 530 comprises a control counter 532 (e.g., a 12-bit counter) with the control clock output 124 being the clock input/trigger to the counter 532 and a measured counter 534 (e.g., a 12-bit counter) with the measured clock output 114 being the clock input/trigger to the counter 534. The comparator circuit further comprises a latch 536 (e.g., 12 D flip-flops).

Accordingly, when the control counter 532 reaches a defined value due to the repeating, periodic clock signal of the controlled clock output 124, the most significant bit of the control counter 532 is switched from digital logic 0 to digital logic 1 (e.g., a low-to high-transition). This output Q12 (MSB) on the control counter 532 operates to control both the reset pin of the measured counter 534 and the clock pin of the latch 536.

As such, the configuration of comparator circuit 530 causes the time period, over which the counting of pulses on the measured clock output 114 occurs, to be a duration that concludes with the MSB or Q12 output of the control counter 532 becoming a digital logic 1 (e.g., high). The Q12 output of the control counter 532 can then first trigger the clock pin of the latch 536, and then the reset pin of the measured counter 534. These operations load the count on the counter 534 into the latch 536 to be used as the salinity measurement 132.

Figure 5B:
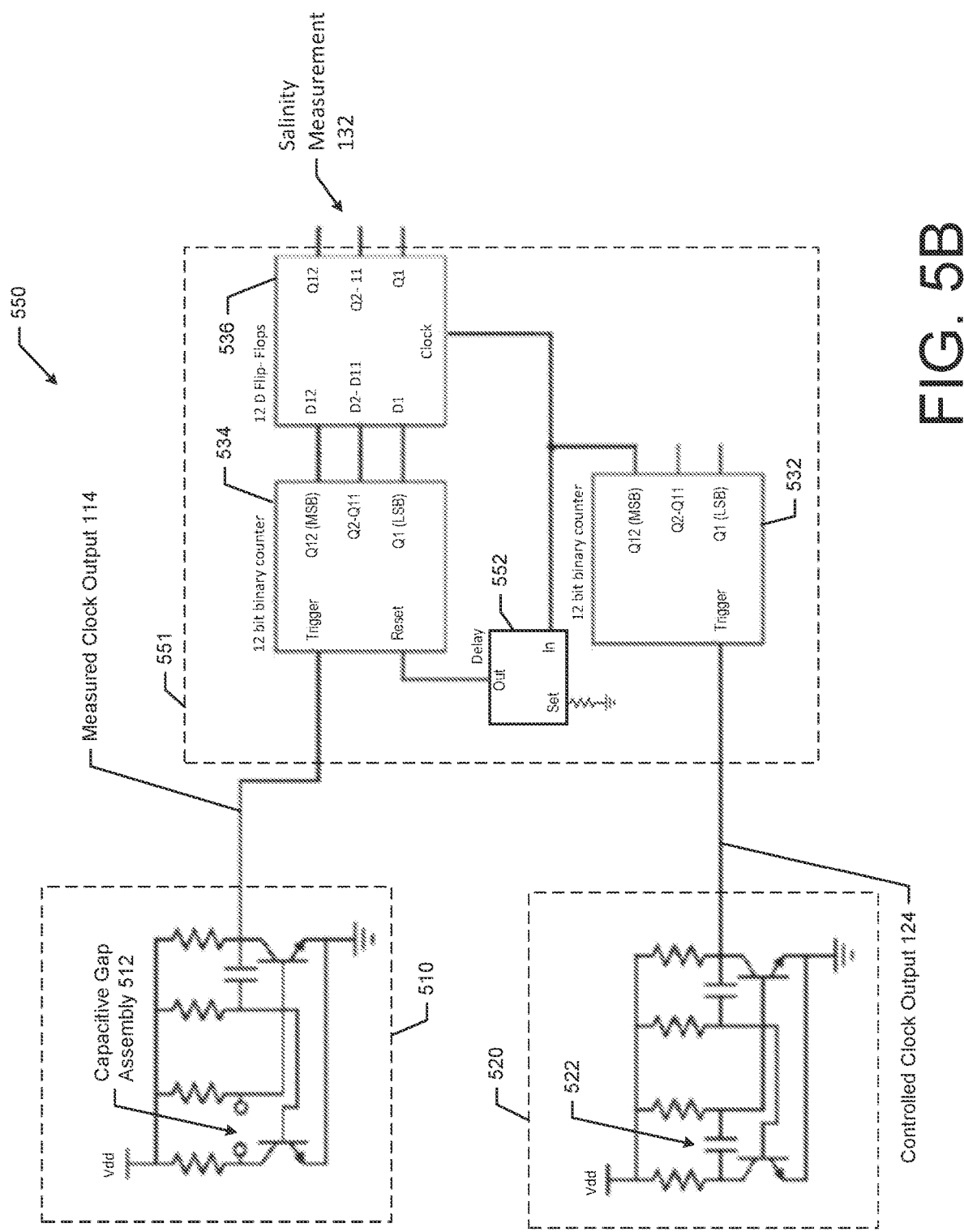
FIG. 5B illustrates a schematic diagram for another salinity sensor comprising a delay component according to some example embodiments.

Now referring to FIG. 5B, another example salinity sensor 550 is provided. The salinity sensor 550 is similar to the salinity sensor 500. Relative to the configuration of the comparator circuit 530, the comparator circuit 551 has the addition of a delay component 552. The delay component 552 may operate to mitigate a race condition that can occur between the clock input of the latch 536 and the reset input of the measured counter 534.

Referring back to FIG. 5A, when the MSB or Q12 of counter 532 turns to a digital logic 1 (e.g., high), the clock pin on the latch 536 should be triggered prior to the reset pin of the counter 534 being triggered. Since these pins are both connected to the same source, a timing or race condition can arise since it is unpredictable which trigger event may occur first. According to some example embodiments, the timing of this sequence of events can be necessary since triggering the clock pin of the latch 536 first, saves the numerical count present in the measured counter 534 before the count is reset by the counter 534.

If the timing of these events is not addressed, it is possible that the electrical signal from the Q12 output of the control counter 532 could first reach the reset pin of the measured counter 534, before the signal reaches the clock pin of the latch 536. In this case, the count in the measured counter 534 may reset to some default value (e.g., zero) and then this default value will be latched or saved in the latch 536, not the original, correct measurement count. As such, the salinity measurement 132 that is saved may be invalid.

Such a race condition may be mitigated in a number of different ways. For example, as provided in the salinity sensor 550 and comparator circuit 551 in FIG. 5B, a delay component 552 may be employed. The delay component 552 may be configured to receive an input at the In pin and provide the same signal, delayed by some delay duration of time, as the output at the Out pin. According to some example embodiments, the delay component 552 may be a digital delay component that provides digital logic output, based on the digital logic input, after a delay duration. The delay duration of time may be configurable, for example, based on the resistance value for a resistor connected to ground at the Set pin of the delay component 552. According to some example embodiments, the delay duration of time may be, for example, twenty microseconds.

As such, the delay component 552 may provide a time offset to the trigger signal coming from the Q12 output of control counter 532 to create a new delayed signal at the reset pin of the counter 534. As such, the trigger signal from Q12 may drive the clock pin of the flip-flops 536 to latch and save the count on the counter 534, and then subsequently, after the delay duration introduced by the delay component 552, the delayed signal provided to the reset pin of the measured counter 534 triggers a reset of the counter 534. In this manner, it is ensured that the reset pin of the measured counter 534 is triggered later in time than the clock pin of the flip-flop 536, thereby mitigating the race condition.

As such, according to some example embodiments, the control counter output (e.g., Q12 of control counter 532) may trigger the latch 536 (e.g., flip-flops) to load the measured count from the measured counter 534 prior to triggering the measured counter 534 to reset. Further, the delay component 552, which may be digital delay component, configured to delay provision of the control counter output (e.g., Q12 of control counter 532) and triggering the measured counter 534 to reset by a delay duration such that the latch 536 to load the measured count is triggered prior to triggering the measured counter 534 to reset.

Figure 6:
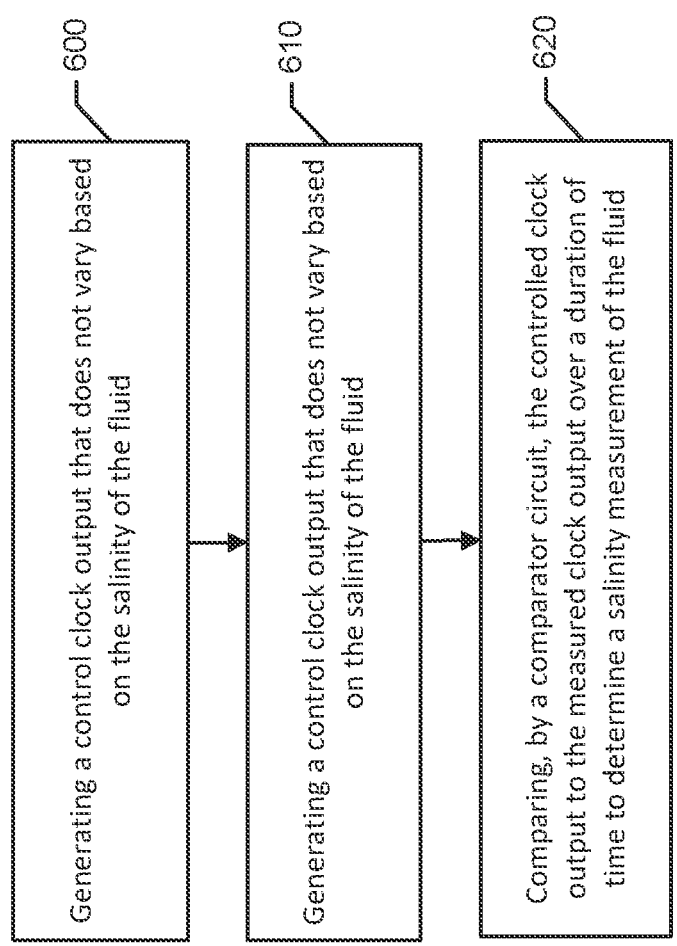
FIG. 6 illustrates a flow chart of an example method for implementing a salinity sensor according to some example embodiments.

With reference to FIG. 6, an example method for measuring salinity in a fluid is provided. In this regard, at 600, the example method may comprise generating a measured clock output that varies based on a salinity of a fluid disposed within a gap between two electrodes of a capacitive gap assembly. The measured clock output may be generated by a measurement clock circuit having a first circuit architecture comprising the capacitive gap assembly. The example method may also comprise, at 610, generating a control clock output that does not vary based on the salinity of the fluid. The control clock output may be generated by a control clock circuit having a second circuit architecture comprising a capacitor. According to some example embodiments, the first circuit architecture may differ from the second circuit architecture in that an electrically connected position of the capacitive gap assembly within the first circuit architecture is the electrically connected position of the capacitor within the second circuit architecture. The example method may further comprise, at 620, comparing, by a comparator circuit, the controlled clock output to the measured clock output over a duration of time to determine a salinity measurement of the fluid. According to some example embodiments, each of the two electrodes of the capacitive gap assembly may be coated by a hydrogel material. Additionally or alternatively, according to some example embodiments, the first circuit architecture may be an astable multivibrator circuit and the second circuit architecture may be an astable multivibrator circuit.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A sensor for measuring ocean water salinity, the sensor comprising:
    a measurement clock circuit having a first circuit architecture comprising a capacitive gap assembly that permits a fluid to flow into a gap between two electrodes of the capacitive gap assembly, the measurement clock circuit having a measured clock output that varies with a salinity of the fluid;
    a control clock circuit having a second circuit architecture comprising a capacitor, the control clock circuit having a controlled clock output that does not vary with the salinity of the fluid; and a comparator circuit configured to compare the controlled clock output to the measured clock output over a duration of time to determine a salinity measurement of the fluid;

wherein the first circuit architecture differs from the second circuit architecture in that an electrically connected position of the capacitive gap assembly within the first circuit architecture is the electrically connected position of the capacitor within the second circuit architecture.

2. The sensor of claim 1 wherein the first circuit architecture is an astable multivibrator circuit and the second circuit architecture is an astable multivibrator circuit.

3. The sensor of claim 1 wherein a frequency of the measured clock output is based on a capacitance between the two electrodes which changes in response to changes in a salinity of the fluid within or around the gap.

4. The sensor of claim 1 wherein the two electrodes of the capacitive gap assembly are two parallel plates.

5. The sensor of claim 1 wherein each of the two electrodes is coated with a hydrogel material.

6. The sensor of claim 5 wherein the hydrogel material comprises carbon nanotubes that create an associated surface charge area for space charge formation.

7. The sensor of claim 1 wherein the comparator circuit comprises a network of binary counters configured to determine a difference between a number of clock pulses in the measured clock output over the duration of time and a number of clock pulses in the controlled clock output over the duration of time.

8. The sensor of claim 1 wherein the measurement clock circuit, the control clock circuit, and the comparator circuit do not comprise a microprocessor or a unitary oscillator.

9. The sensor of claim 1 wherein the comparator circuit comprises a measured counter, a control counter, and a latch;
wherein the measured clock output is an input to the measured counter;
wherein the control clock output is an input to the control counter;
wherein a control counter output controls the latch to load a measured count accumulated by the measured counter based on the measured clock output into the latch.

10. The sensor of claim 9 wherein the control counter output also resets the measured counter.

11. The sensor of claim 10, wherein the control counter output triggers the latch to load the measured count prior to triggering the measured counter to reset.

12. The sensor of claim 11 further comprising a digital delay component configured to delay, by a delay duration, provision of the control counter output to the measured counter to reset the measured counter such that the latch is triggered to load the measured count prior to triggering the measured counter to reset.

13. A sensor for measuring ocean water salinity, the sensor comprising:
a capacitive gap assembly comprising two electrodes that form a gap there between; and
a salinity measurement apparatus operably coupled to the capacitive gap assembly, the salinity measurement apparatus configured to determine a salinity measurement of a fluid disposed in the gap between the two electrodes based on a displacement current between the electrodes;
wherein the electrodes are coated with a hydrogel material.

14. The sensor of claim 13 wherein the salinity measurement apparatus comprises:
a measurement clock circuit having a first circuit architecture operably coupled to the capacitive gap assembly, the measurement clock circuit having a measured clock output that varies with a salinity of the fluid;
a control clock circuit having a second circuit architecture operably coupled to a capacitor, the control clock circuit having a controlled clock output that does not vary with the salinity of the fluid; and
a comparator circuit configured to compare the controlled clock output to the measured clock output over a duration of time to determine the salinity measurement of the fluid;
wherein the first circuit architecture differs from the second circuit architecture in that an electrically connected position of the capacitive gap assembly within the first circuit architecture is the electrically connected position of the capacitor within the second circuit architecture.

15. The sensor of claim 14 wherein the first circuit architecture is an astable multivibrator circuit and the second circuit architecture is an astable multivibrator circuit.

16. The sensor of claim 14 wherein the hydrogel material is configured to inhibit marine fouling of the two electrodes.

17. The sensor of claim 14 wherein the hydrogel material comprises conductive fillers, dyes, or additives.

18. The sensor of claim 13 wherein the two electrodes comprise a first electrode and a second electrode, and the hydrogel material fills the gap extending from the first electrode through the gap to the second electrode.

19. The sensor of claim 13 wherein the two electrodes of the capacitive gap assembly are two parallel plates.

20. A method comprising:
generating a measured clock output that varies based on a salinity of a fluid disposed within a gap between two electrodes of a capacitive gap assembly, the measured clock output being generated by a measurement clock circuit having a first circuit architecture comprising the capacitive gap assembly;
generating a control clock output that does not vary based on the salinity of the fluid, the control clock output being generated by a control clock circuit having a second circuit architecture comprising a capacitor, wherein the first circuit architecture differs from the second circuit architecture in that an electrically connected position of the capacitive gap assembly within the first circuit architecture is the electrically connected position of the capacitor within the second circuit architecture; and
comparing, by a comparator circuit, the controlled clock output to the measured clock output over a duration of time to determine a salinity measurement of the fluid.

21. The method of claim 20 wherein each of the two electrodes is coated by a hydrogel material.

22. The method of claim 20 wherein the first circuit architecture is an astable multivibrator circuit and the second circuit architecture is an astable multivibrator circuit.

* * * * *